US00PP13294P3

(12) United States Plant Patent
DePew et al.

(10) Patent No.: US PP13,294 P3
(45) Date of Patent: Dec. 3, 2002

(54) SEASHORE PASPALUM 'SDX-1'

(76) Inventors: Michael DePew, 835 Herricksville Rd., Tekonsha, MI (US) 49092; Stewart Bennett, 14261 Clubhouse Dr., Bokeelia, FL (US) 33922; Paul H. Tillman, 14261 Clubhouse Dr., Bokeelia, FL (US) 33922

( * ) Notice: Subject to any disclaimer, the term of this patent is extended or adjusted under 35 U.S.C. 154(b) by 0 days.

(21) Appl. No.: 09/759,481

(22) Filed: Jan. 12, 2001

(65) Prior Publication Data

US 2002/0095707 P1 Jul. 18, 2002

(51) Int. Cl.[7] ..... A01H 5/00
(52) U.S. Cl. ..... Plt./388
(58) Field of Search ..... Plt./388

(56) References Cited

PUBLICATIONS

U.S. patent application Ser. No. 09/643,598, DePew, et al., filed Aug. 22, 2000.
U.S. patent application Ser. No. 09/643,286, DePew, et al., filed Aug. 22, 2000.
U.S. patent application Ser. No. 09/502,904, Bennett, et al., filed Feb. 11, 2000.
U.S. patent application Ser. No. 09/502,903, Bennett, et al., filed Feb. 11, 2000.
R. Duncan, "Environmental Compatibility of Seashore Paspalum for Golf Courses and Other Recreational Uses," ITS paper, 21 pages (Jul. 1997).
Brochure for Sweet ADALAYD, 2 pages (1980–1983?).
R. Duncan, "Development of Stress Tolerant Seashore Paspalum for Golf Course Usage," Preliminary Progress Report, University of Georgia, 8 pages (May 1993).
J. Morton, "Salt–Tolerant Silt Grass (*Paspalum Vaginatum* SW.)," *Florida State Horticultural Society,* 482–490 (1973).
D. Guiot, et al. "Salty But Rarely Off Color," 2 pages (1980–1983?).
R. Duncan, "Development of Multiple Stress Tolerant Seashore Paspalums for Golf Course Usage," USGA Annual Report, 7 pages (1996).
"Grass Experiment a Hit at Alden Pines," 2 pages (1980–1983).
"'SALAM' Seashore Paspalum" web page (www.woerner.com/wmpage/wsti/salam.htm) (1 pg) (Jan. 1998).
Z. Liu, et al., "Characterization and Analysis of Simple Sequence Repeats (SSR) Loci in Seashore Paspalum," (www.nal.usda.gov/ttic/tektran/data), 2 pages (Jan. 21, 1998).

*Primary Examiner*—Bruce R. Campell
*Assistant Examiner*—Annette H. Para
(74) *Attorney, Agent, or Firm*—Laura G. Barrow

(57) ABSTRACT

A novel seashore paspalum cultivar (*Paspalum vaginatum*) is disclosed. The 'SDX-1' cultivar is characterized by having a fine texture, greater sod strength, increased rooting, improved color, improved density, and greater salinity tolerance. The cultivar is particularly well suited for golf courses, grass tennis lawns, lawn bowls, lawns, and athletic fields.

6 Drawing Sheets

SUMMARY OF THE INVENTION

The present invention relates to a new cultivar of seashore paspalum (*Paspalum vaginatum* Swartz) that is particularly suited as a turf grass for recreational fields and golf courses. The new cultivar of the present invention is herein referred to by its cultivar name 'SDX-1'.

The 'SDX-1' cultivar is a low growing halophytic grass spreading by rhizomes and stolons. The 'SDX-1' cultivar exhibits a dwarf growth habit that seldom exceeds two inches in mature height under conditions of full sun. The grass is particularly well suited for use on golf courses for putting greens mowed to ⅛ inch and for fairways mowed to ¼ inch. It is also suitable for lawns, grass tennis courses, lawn bowls, athletic fields or any other area where a fine textured close mown and low growing turf with superior salt tolerance is desired.

DETAILED DESCRIPTION OF THE VARIETY

Figure 1:
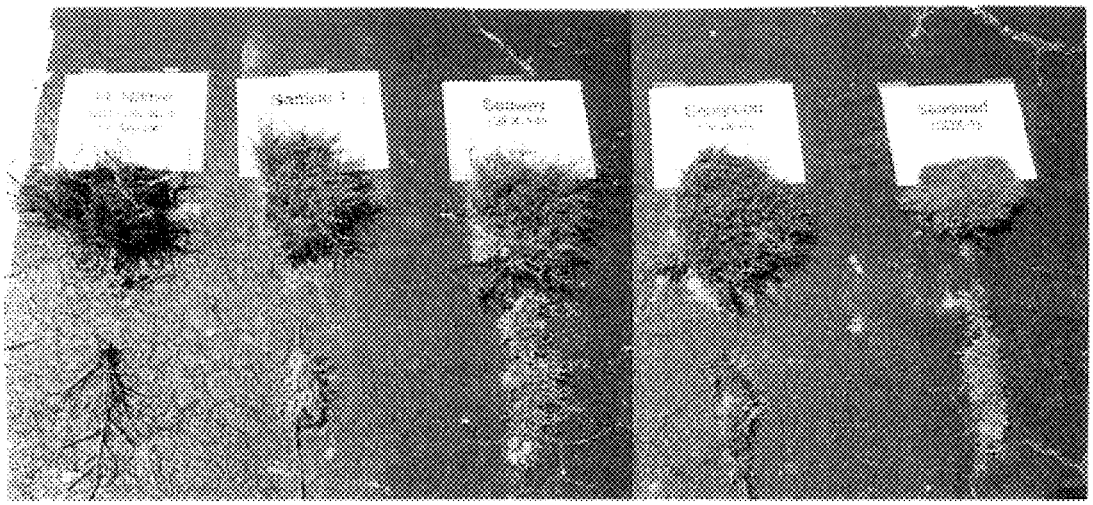
FIG. 1 shows a comparison of the inventive cultivar with a Florida native (natural) ecotype and four improved turf-type varieties. These varieties, from left to right, are Florida native type, 'SeaIsle 1' (University of Georgia release), Applicants' variety 'SFX-14' (Ser. No. 09/502,903), Applicants' variety 'SGX-6' (Ser. No. 09/502,904), and Applicant's seashore paspalum variety named 'SDX-1'.
Figure 2:
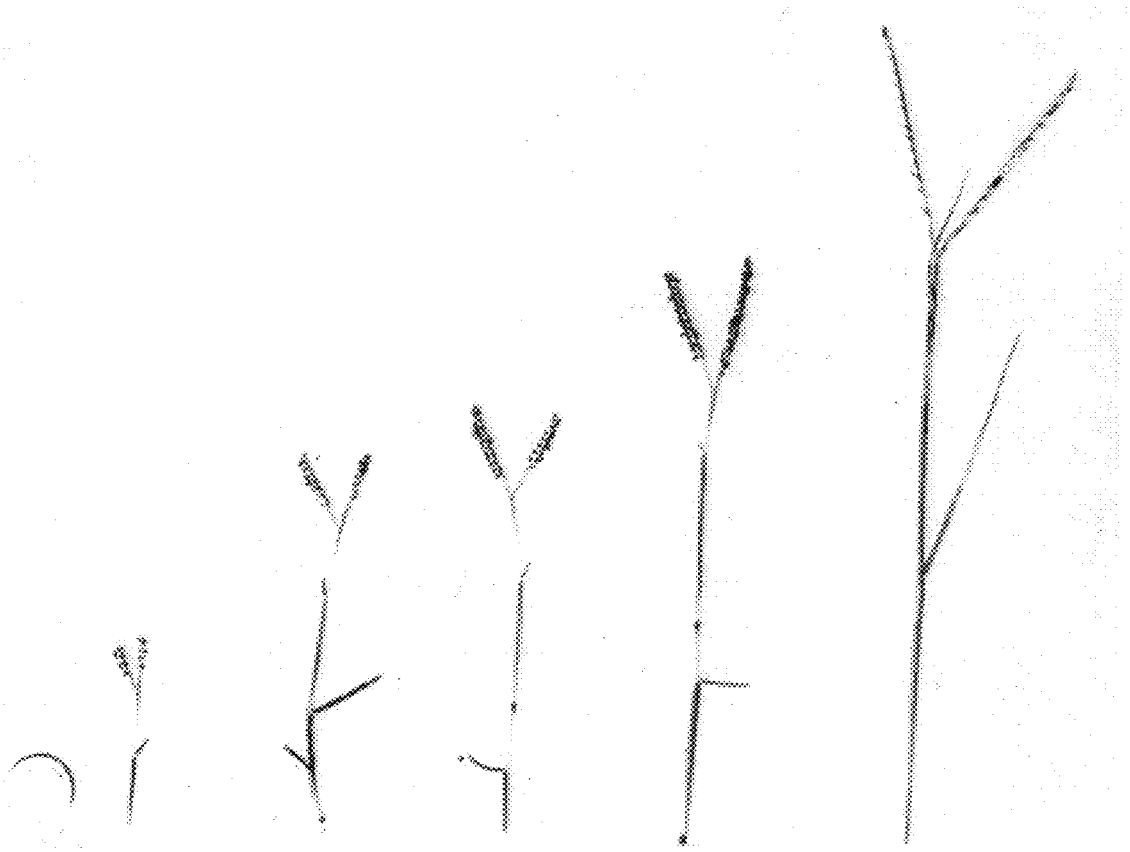
FIG. 2 shows seedheads form various seashore paspalum varieties. These varieties, from left to right, are Florida native type, 'SeaIsle 1' (University of Georgia release), Applicants' variety 'SFX-14', Applicants' variety 'SGX-6', and Applicant's seashore paspalum variety named 'SDX-1'.
Figure 3:
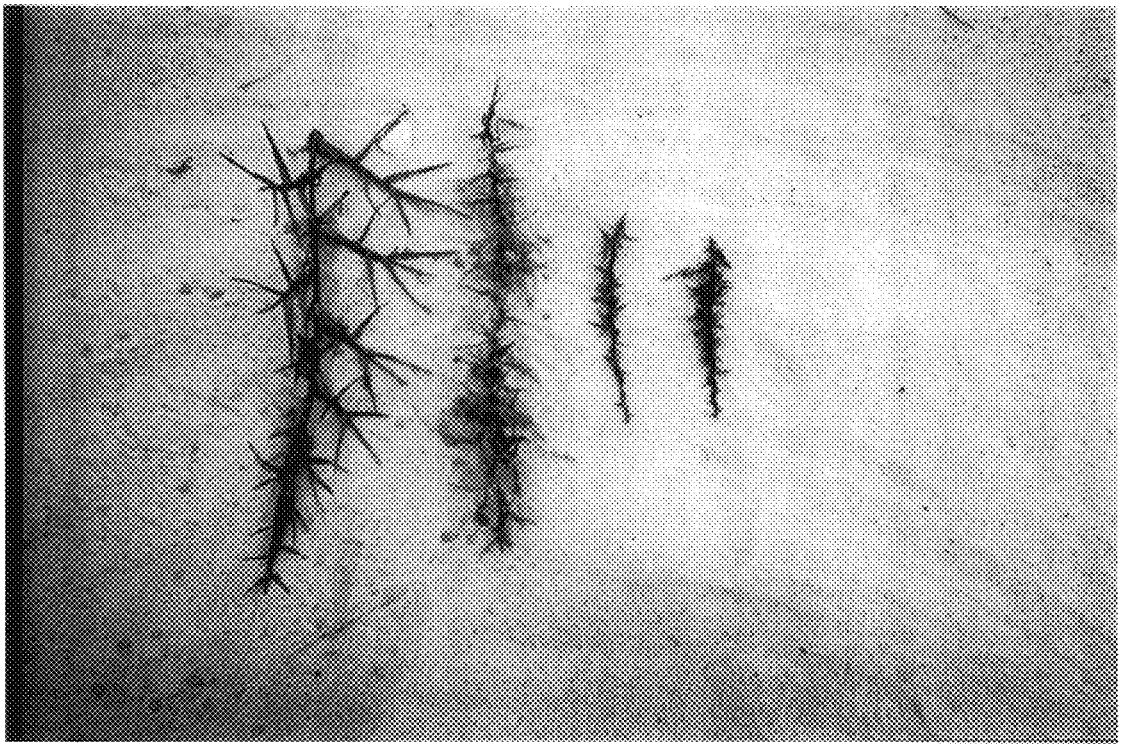
FIG. 3 is a photograph of stolon sprigs of the 'SDX-1' variety (#4) compared to other seashore paspalum varieties (#1=native seashore paspalum; #2=applicants' 'SFX-14' variety; and #3=applicants' 'SGX-6' variety).
Figure 4:
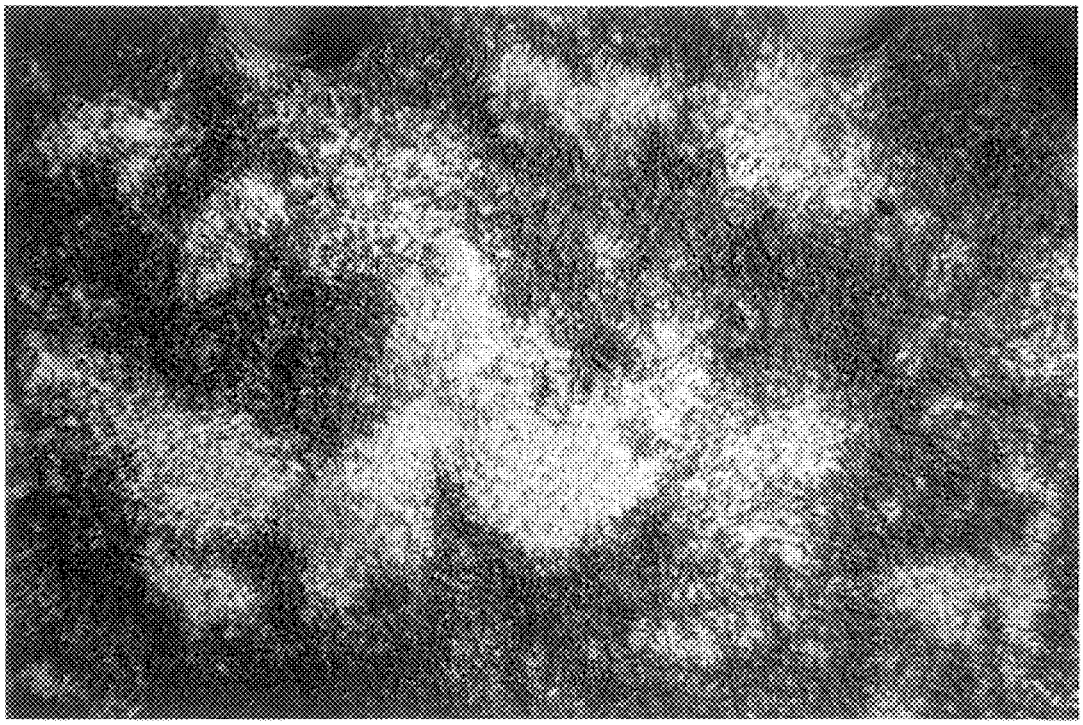
FIG. 4 is a photograph of the 'SDX-1' variety 4 weeks following sprigging.
Figure 5:
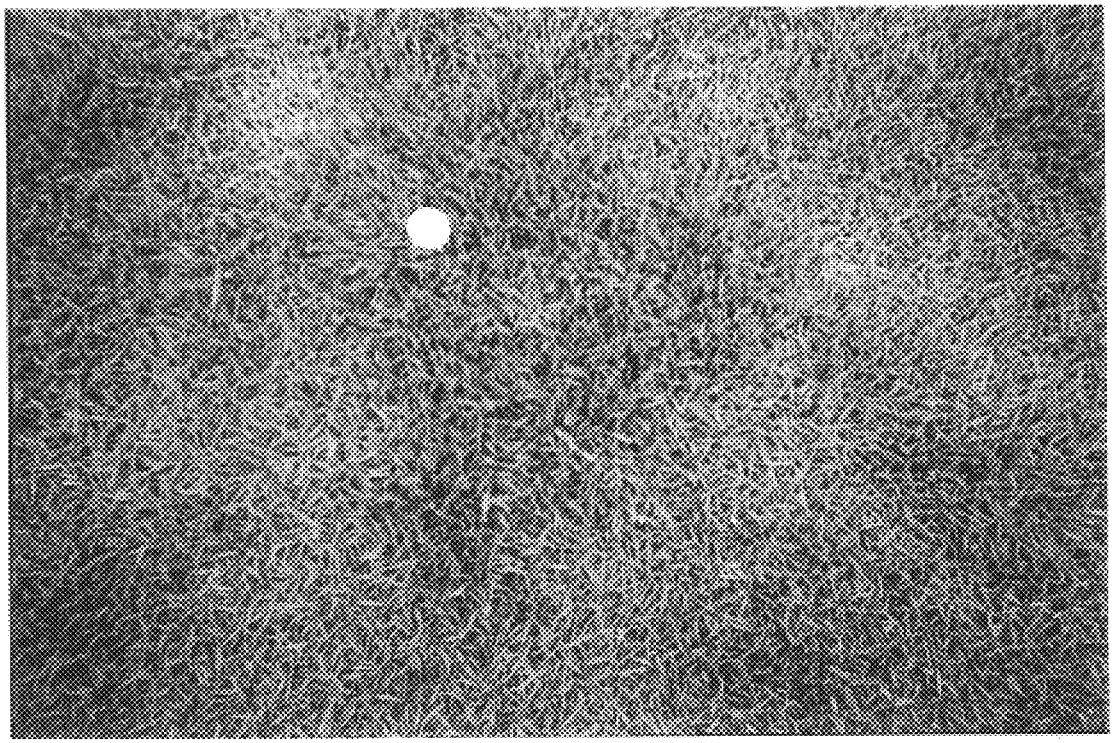
FIG. 5 is a photograph of the 'SDX-1' variety (unmown) 12 weeks following sprigging.
Figure 6:
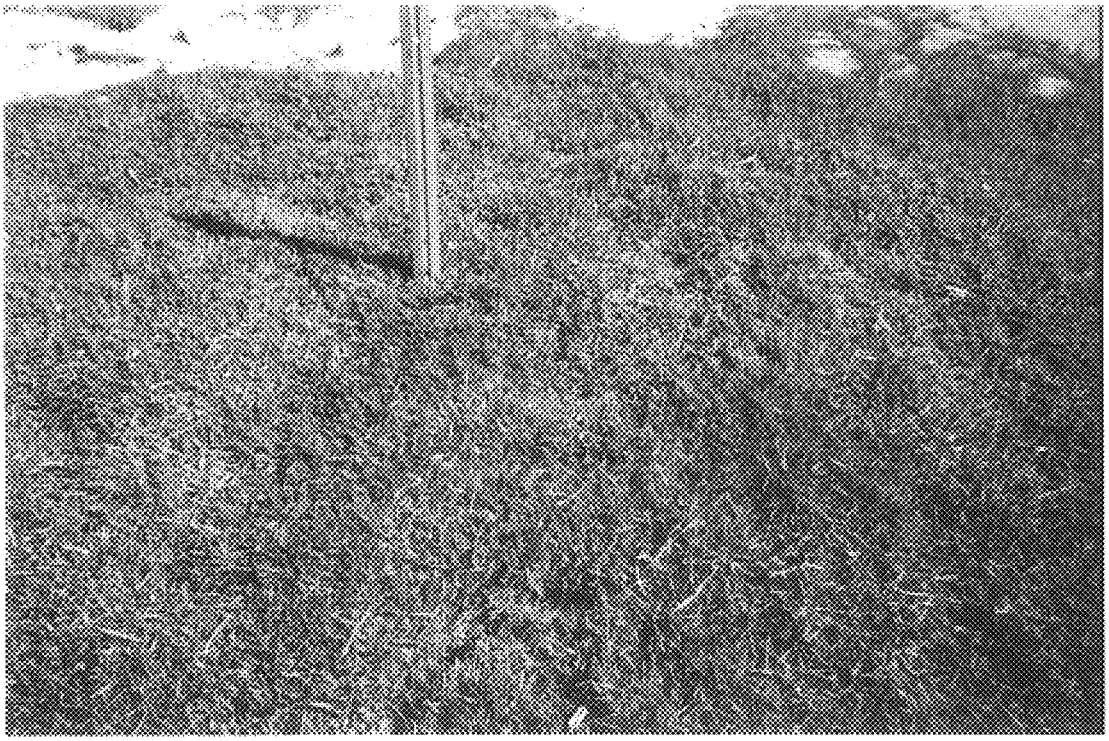
FIG. 6 is a photograph of the 'SDX-1' variety (unmown) 32 months following establishment.

The following is a detailed description of the new grass variety based upon observation of the grass grown in field plots and under live golf conditions on a local golf course.

Asexual Reproduction

The 'SDX-1' grass was developed by the applicants on Pine Island, Fla. in a saline environment. Early ecotypes from the applicants' turf development program were developed from crosses between Florida native ecotypes and 'Adalayd' (U.S. Plant Pat. No. 3,939) seashore paspalum. 'SDX-1' was developed by crossing applicants' improved turf-type ecotypes and subsequent evaluation of the resulting progeny. Trial areas of the grass were established and maintained under live golf conditions at Alden Pines Country Club, Bokeelia, Fla. (a salt water irrigated golf course) since 1997. This grass has been asexually propagated by the applicants as sprigs, plugs, and sod, and remain true to type in subsequent asexual reproductions, subject to damage from external factors, as discussed further below.

Botanical description

The age of the cultivar observed for the following botanical description was about 180 days. All color descriptions with respect to parts of the cultivar, where color is a distinguishing feature, are made to the Munsell Color Chart, except where terms of ordinary usage and dictionary meaning are used. The 'SDX-1' cultivar is a perennial grass. The grass stems have overlapping sheath margins and arise from an extensive system of long, straw colored, slender rhizomes and/or purple-tinged stolons. The grass blades are glabrous and folded, forming a V-shape. The grass blades have an olive green color, Munsell color designation 7.5 GY 4/6 (abaxial side) and 7.5 GY 5/4 (adaxial side). The blade length is generally 0.5–1.6 cm (unmown). The blades have a typical width of from 1.75 to 3.0 mm, varying with the level of salinity and tapering to an involute apex. Leaf-blade venation runs parallel without cross veins. The veins are obscure with a prominent mid-vein. The leaf margins are smooth. Leaf-sheath auricles are absent. The ligules have an eciliate membrane. External ligules are not present on the collar. Upon flowering, the culms are about 0.5–4.5 cm tall (most are 1.5–2.5 cm tall) with terminal inflorescence subtended by an unspecialized leaf-sheath. Inflorescence bears well-developed spikelets forming paired branches (racemes) at the culm apex about 0.6–1.6 cm in length. The racemes each have a broad, triangular rachis bearing two rows of spikelets (one floret per spikelet). The rachis are angular and narrowly winged. The rachis, which are tough and persistent, are also about 1–2 mm in width, and terminate in a spikelet. Spikelet packing is regular, two-rowed, abaxial, and contiguous, with subequal internodes.

Florets (seed) are ovate and about 0.4–0.75 mm in diameter. Glumes, palea, and lemma are awnless, glabrous, and green with an acute apex.

Leaf blade with and length of the 'SDX-1' cultivar are affected by both salinity level and by the length of sunlight exposure. It produces longer narrower leaf blades in winter compared to shorter, wider leaf blades in summer. Likewise, as salinity levels increase, shorter, narrower, and somewhat more erect leaf blades are produced, compared to longer wider blades produced upon irrigation with a fresh water or low salinity system.

General Observations

This grass has shown to be particularly well suited for use on putting green surfaces due to the high shoot density, short internode length, short blades and fine texture produced under close mown conditons and saline irrigation. Due to its inherent dwarf growth form, this grass is also suited for use on high-quality lawn areas where an infrequent mowing regime is utilized, seldom exceeding 2 inches in overall height under unmown conditions in full sunlight. While 'SDX-1' exhibits dwarf growth form with short internode length and overall low vertical growth habit, the grass grows very vigorously and densely in a horizontal fashion and quickly forms a dense sod when established from sprigs. This grass has been tested under regular saline irrigation up to 26,000 ppm. Trials have been conducted applying 45,000 ppm (brine) salinity water to putting green surfaces established with this grass for weed and pest control. Target organisms have been eliminated with the brine water application with no apparent visual damage to the grass. Direct applications of table salt or sea salt has also been employed for weed control although temporary burning of the grass leaf tips may be observed with heavy salt applications.

SDX-1 develops an extensive rhizome system composed of primary rhizomes, with secondary and tertiary rhizome branches arising from the primary rhizomes. As the turf stand matures, the primary rhizomes will store appreciable carbohydrate reserves and become thickened and somewhat tuberous with the leaf shoots typically originating exclusively from the secondary and tertiary rhizome system. In the event that the turf is damaged such that loss of leaf shoots and rhizome branches occur, new leaf shoots may be initiated from nodes on the primary rhizomes. If such an event does occur, the initial leaf shoots arising from the thickened primary rhizomes will initially be larger and coarser than leaf shoots typical of the SDX-1 cultivar. As the turf recovers from the damage, and new rhizome branches are developed, the resultant leaf shoots will be typical of the SDX-1 cultivar as described. Restoration of the fine-textured leaf shoot system typical of the SDX-1 cultivar may be enhanced by common turf cultural practices, such as mowing and verti-cutting.

Damage to the turf that may result in leaf shoots emerging from primary rhizomes typically includes insect damage, disease damage, or damage from chemical burning (e.g. oil spill).

Thickened, primary rhizomes as described are typically 4 to 5 mm in diameter. Leaf blades from any emerging leaf shoots arising from such rhizomes are from about 4 to 5 mm in width, corresponding to the diameter of rhizome, and about 2 to 3 cm in length. Secondary rhizome branches are typically 1.5 to 3 mm in diameter, and tertiary rhizome branches are typically 0.75 to 1.5 mm in diameter. The primary rhizomes typically develop with some depth in the soil profile, from 4.75 to 10 cm in depth (occasionally up to 15 cm depth). Secondary and tertiary rhizome branches develop throughout the rhizome profile depth, with leaf shoot initiation typically restricted to those rhizomes within the 0 to 4 cm soil profile depth range.

Compared to 'Adalayd' ('Excalibre') seashore paspalum utilized for similar purposes, this grass has foremost greater salinity tolerance, and under saline conditions, improved density, finer texture, greater sod strength, increased rooting and improved color. Compared to other seashore paspalum turfgrass ecotypes developed by the applicants', 'SDX-1' is a compact, dwarf form that forms a low, dense, tight sod even under unmown conditions. Compared to other fine textured grass species (notably common and hybrid bermudagrass) for similar use, this grass has adaptations for moderate shade tolerance and enhanced temperature tolerance, retaining color at lower temperatures than bermudagrasses. This grass has a lower water use requirement compared to St. Augustine and hybrid bermudagrass cultivars and has enhanced qualities for drought tolerance and can be grown in sandy soils as well as in heavy-textured waterlogged soils.

We claim:

1. A new and distinct cultivar of seashore paspalum grass, substantially as herein illustrated and described, characterized by its fine texture when closely mown, its superior tolerance to salt, drought, and soil hypoxic conditions, and its low, dwarf growth habit even under unmown conditions.

* * * * *